United States Patent
Routray et al.

(10) Patent No.: US 11,593,814 B2
(45) Date of Patent: Feb. 28, 2023

(54) ARTIFICIAL INTELLIGENCE FOR ROBUST DRUG DILUTION DETECTION

(71) Applicant: International Business Machines Corporation, Armonk, NY (US)

(72) Inventors: Ramani R. Routray, San Jose, CA (US); Venkat K. Balagurusamy, Suffern, NY (US); Ashwin Dhinesh Kumar, Ossining, NY (US); Donna N Eng Dillenberger, Yorktown Heights, NY (US); Bruce Light Hillsberg, San Carlos, CA (US); Mark Dudman, Seabrook Beach, NH (US)

(73) Assignee: MERATIVE US L.P., Ann Arbor, MI (US)

( * ) Notice: Subject to any disclaimer, the term of this patent is extended or adjusted under 35 U.S.C. 154(b) by 414 days.

(21) Appl. No.: 16/851,531

(22) Filed: Apr. 17, 2020

(65) Prior Publication Data
US 2021/0326900 A1   Oct. 21, 2021

(51) Int. Cl.
*G06K 9/00* (2022.01)
*G06Q 30/018* (2023.01)
*G06N 20/00* (2019.01)
*G06N 3/088* (2023.01)
*G16H 50/20* (2018.01)
(Continued)

(52) U.S. Cl.
CPC ....... *G06Q 30/0185* (2013.01); *G06K 9/6256* (2013.01); *G06N 3/088* (2013.01);
(Continued)

(58) Field of Classification Search
CPC . G06T 2207/20081; G06T 2207/30108; G06T 2207/30128; G06T 7/0004;
(Continued)

(56) References Cited

U.S. PATENT DOCUMENTS

2005/0077476 A1   4/2005  Poteet et al.
2010/0305499 A1   12/2010 Matsiev et al.
(Continued)

OTHER PUBLICATIONS

B. McKenzie, et al., "Chronoprints: Identifying Samples by Visualizing How They Change over Space and Time", ACS Cent. Sci. 2019, 5, 589-598, Mar. 20, 2019, 10 pages.
(Continued)

*Primary Examiner* — Atiba O Fitzpatrick
(74) *Attorney, Agent, or Firm* — Edell, Shapiro & Finnan, LLC

(57) ABSTRACT

Techniques are provided detecting diluted drugs using machine learning. Measurements and images corresponding to a product are obtained, wherein the product is formulated as a liquid, and wherein the measurements and images capture physical, spectral, optical, and/or chemical properties of the product. The measurements and images are provided to a machine learning model, wherein the machine learning model is trained using data generated from interactive learning modules (e.g., a generative adversarial network). The machine learning model detects whether the product or chemical is a real or counterfeit product. In addition, these techniques may be used by practitioners (e.g., medical personnel dispensing a prescribed dosage of a drug with a specific dilution level) to detect prescription errors at the point of administration.

20 Claims, 10 Drawing Sheets

(51) Int. Cl.
  *G06K 9/62* (2022.01)
  *G16H 20/10* (2018.01)
  *G06V 30/24* (2022.01)

(52) U.S. Cl.
  CPC ......... *G06N 20/00* (2019.01); *G06V 30/2504* (2022.01); *G16H 20/10* (2018.01); *G16H 50/20* (2018.01)

(58) Field of Classification Search
  CPC ........ G06T 7/0002; G06N 3/08; G06N 3/088; G06V 10/774; G06V 20/95; G06K 9/6256; G06Q 30/0185; G06Q 30/018; G16H 20/10; G16H 20/00; G16H 20/60; G16H 70/40
  See application file for complete search history.

(56) References Cited

U.S. PATENT DOCUMENTS

| | | |
|---|---|---|
| 2014/0154813 A1 | 6/2014 | Decoux et al. |
| 2015/0269593 A1 | 9/2015 | Le |
| 2019/0197358 A1* | 6/2019 | Madani ................. G06T 7/0012 |
| 2019/0197368 A1* | 6/2019 | Madani ................. G06N 3/082 |
| 2019/0198156 A1* | 6/2019 | Madani ................. G06V 10/764 |
| 2019/0236614 A1* | 8/2019 | Burgin .................. G06V 20/80 |
| 2021/0103936 A1* | 4/2021 | Gomes Pereira ...... G16H 40/20 |
| 2022/0076075 A1* | 3/2022 | Madani ................. G06V 10/764 |

OTHER PUBLICATIONS

A. Mishra, et al., "Low-cost spectrogram based counterfeit medicine detection", https://arxiv.org/abs/1904.07152, Apr. 10, 2019, 7 pages.

P. He, et al., "Honey Authentication with Machine Learning Augmented Bright-Field Microscopy", https://arxiv.org/abs/1901.00516v1, Dec. 28, 2018, 6 pages.

W. Herrington et al., "Optical Detection of Degraded Therapeutic Proteins", Scientific Reports (2018) 8:5089, Mar. 23, 2018, 10 pages.

* cited by examiner

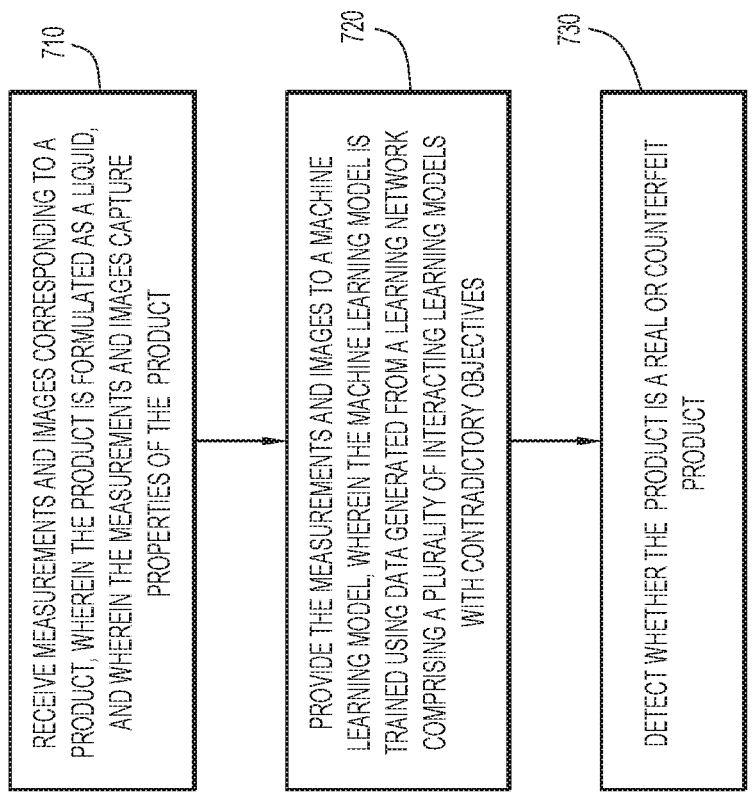

ARTIFICIAL INTELLIGENCE FOR ROBUST DRUG DILUTION DETECTION

1. Technical Field

Present invention embodiments relate to detecting counterfeit pharmaceuticals and biologics, and in particular, to detecting dilutions of liquid formulations, using generative adversarial neural network techniques.

2. Discussion of the Related Art

Counterfeit products are fake or unauthorized replicas of a real product. Such products are illegal and often harmful to health. For instance, counterfeit therapeutics may be contaminated with toxins, bacteria, or other microbes. In other cases, counterfeit therapeutics may contain the wrong ingredient or may not have a sufficient amount of an active ingredient. For instance, the counterfeit medicine may contain the active ingredient but at wrong dose, or may not have any active ingredient at all. Counterfeit products are often substandard products sold beneath market value through illegal sources that are not regulated.

Counterfeit liquid formulations are often replaced with inactive saline liquid or may contain a real therapeutic that is diluted with an inactive ingredient such as saline. Such products may be contained in packaging or vials from the real manufacturer and therefore, may be difficult to detect. In other aspects, the counterfeit therapeutic may be contained in falsified packaging.

SUMMARY

According to embodiments of the present invention, methods, systems, and computer readable media are provided for detecting diluted drugs using machine learning. Measurements and images corresponding to a product are obtained, wherein the product is formulated as a liquid, and wherein the measurements and images capture physical, spectral, optical, and/or chemical properties of the product. The measurements and images are provided to a machine learning model, wherein the machine learning model is trained using data generated from interactive learning modules, such as a generative adversarial network. The machine learning model detects whether the product is a real or counterfeit product.

It is to be understood that the Summary is not intended to identify key or essential features of embodiments of the present disclosure, nor is it intended to be used to limit the scope of the present disclosure. Other features of the present disclosure will become easily comprehensible through the description below.

BRIEF DESCRIPTION OF THE DRAWINGS

Generally, like reference numerals in the various figures are utilized to designate like components.

FIG. 6 shows a high level flowchart for detecting drug dilution, according to an embodiment of the present invention.

DETAILED DESCRIPTION

Detection of diluted counterfeit drugs may be used to validate that a patient receives a dosage of a therapeutic with proper efficacy and at a prescribed value prior to administration. However, detection of diluted drugs is often challenging, as counterfeit drugs may have a similar appearance to real drugs. Additionally, detection of counterfeit drugs using machine learning is often difficult, as a large amount of training data may be needed to achieve a machine learning model with suitable accuracy. Generating such training data using real drugs is both time consuming and expensive.

Present techniques use minimal physical data capture to generate initial seed data provided to a generative adversarial network. The generative adversarial network generates additional training data used to enhance robustness of a drug dilution detection machine learning model. In particular, the generative adversarial network uses a noise vector and captured images to add robustness to the training data to train the drug dilution detection machine learning module.

These techniques provide for technological improvements in data processing and machine learning. For example, the machine learning system may be trained more quickly and efficiently by generating a robust data set from seed data, wherein the seed data comprises measurements of the real product and coarse grained dilutions of the real product. Present approaches provide for the same or similar accuracy as compared to approaches in which the training data set is generated manually. In some cases, properties of the generated data, whether from the fine grained data produced by the counterfeit diluted generator or the generator network, may be stored in a compact format (as compared to an image which may undergo processing to obtain corresponding properties), and therefore, present approaches may utilize less memory than existing approaches.

Figure 1A:
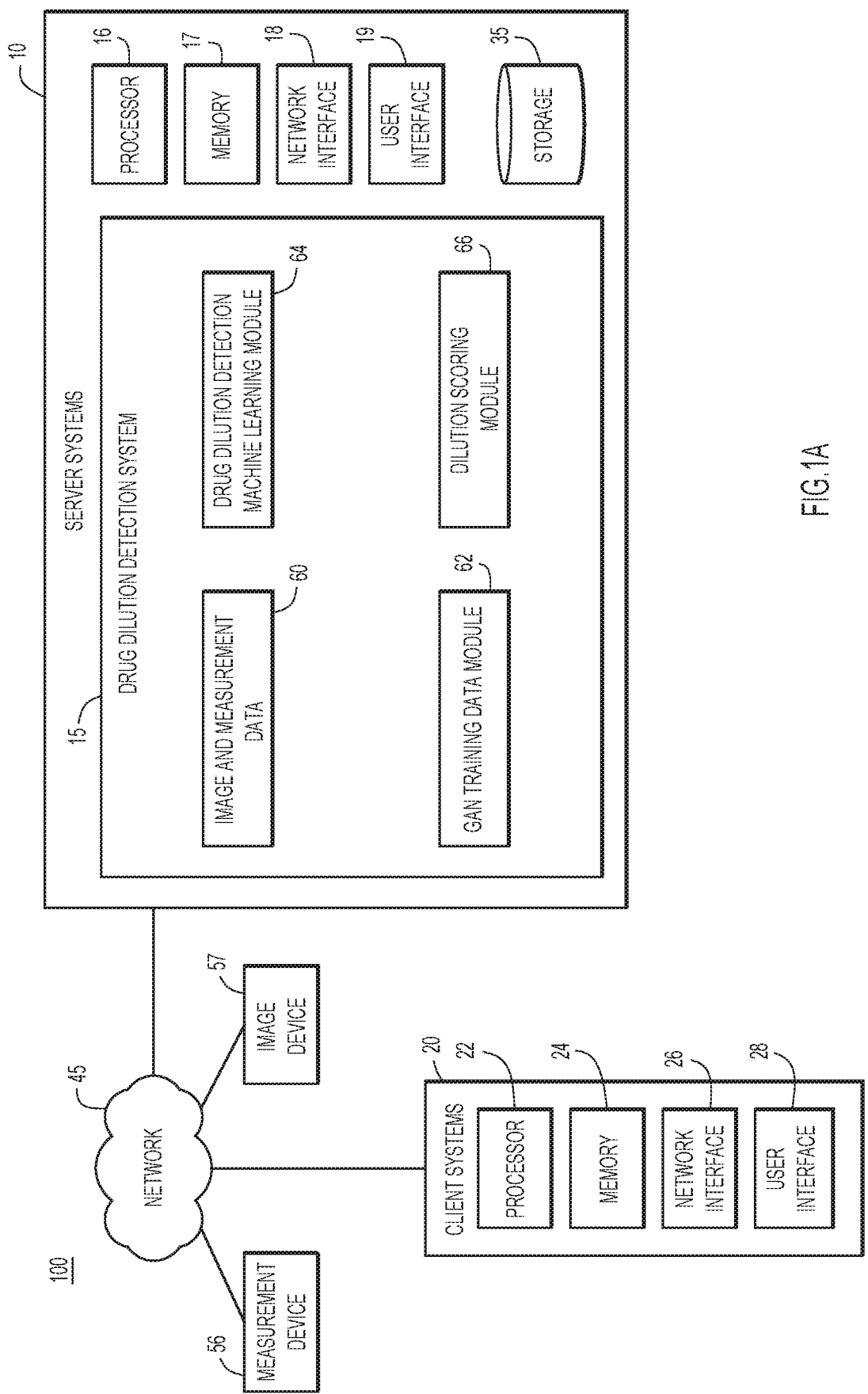
FIG. 1A is a diagrammatic illustration of an example computing environment for a drug dilution detection system, according to an embodiment of the present invention.

An example environment for use with present invention embodiments is illustrated in FIG. 1A. Specifically, the environment includes one or more server systems 10, one or more client or end-user systems 20 and a network 45. Server systems 10 and client systems 20 may be remote from each other and may communicate over network 45. The network may be implemented by any number of any suitable communications media, such as a wide area network (WAN), a local area network (LAN), Internet, Intranet, etc. Alternatively, server systems 10 and client systems 20, may be local to each other, and may communicate via any appropriate local communication medium, such as local area network (LAN), hardwire, wireless link, Intranet, etc.

Client systems 20 enable users to provide information (e.g., measurements and images) to server systems 10 and to obtain results of the analysis from server systems 10.

Server systems 10 may comprise a storage database 35 that may store various types of information (e.g., measurements and images, training data, etc.) for the analysis. Storage 35 may include any suitable information in a structured, semi-structured, or unstructured format, including optical and spectroscopic images (e.g., optical photography, spectroscopy, etc.) as well as physical and chemical measurements (e.g., pH, viscosity, reactivity, etc.).

Storage database 35 may be implemented by any conventional or other database or storage unit, may be local to or remote from server systems 10 and client systems 20 and may communicate via any appropriate communication medium, such as local area network (LAN), wide area network (WAN), Internet, hardwire, wireless link, Intranet, etc. The client systems may present a graphical user interface, such as a GUI, etc., or other interface, such as command line prompts, menu screens, etc., to solicit product inquiries from users, and to detect product integrity.

Server systems 10 and client systems 20 may be implemented by any conventional or other computer systems preferably equipped with a display or monitor, a base (including at least one hardware processor (e.g., microprocessor, controller, central processing unit (CPU), etc.), one or more memories and/or internal or external network interfaces or communications devices (e.g., modem, network cards, etc.), optional input devices (e.g., a keyboard, mouse or other input device), and any commercially available and custom software (e.g., server/communications software, drug dilution detection system software, browser/interface software, etc.). By way of example, the server/client includes at least one processor 16, 22, one or more memories 17, 24 and/or internal or external network interfaces or communications devices 18, 26 such as a modem or network cards, and a user interface 19, 28 etc. The optional input devices may include a keyboard, mouse, or other input device. The client system may be any suitable device, including but not limited to mobile devices, Internet of Things (IoT) devices, and Internet of Bodies (IoB) devices, tablets, etc. or any other device capable of obtaining images or measurements of a product and sending the information via a local or wide area network to a drug dilution detection system 15 for analysis.

Alternatively, one or more client systems 20 may perform the operations of servers systems 10 in a stand-alone mode of operation. For example, the client system may store or have access to drug dilution detection system 15. The graphical user or other interfaces 19, 28, such as a GUI, command line prompts, menu screens, etc., solicits product inquiries from corresponding users regarding drugs, and may provide reports or other information including whether the product is a real drug or a counterfeit (diluted) drug.

Drug dilution detection system 15 may include one or more modules or units to perform the various functions of present invention embodiments described herein. The various modules (e.g., drug dilution detection system 15, comprising image and measurement data module 60, generative adversarial neural network (GAN) training data module 62, drug dilution detection machine learning module 64, and dilution scoring module 66, etc.), may be implemented by any combination of any quantity of software and/or hardware modules or units, and may reside within memory 17 of the server for execution by processor 16. These modules are described in additional detail below.

Image and measurement data module 60 receives various types of data for training the drug dilution detection system 15. Data may encompass any physical, chemical, spectroscopic and/or optical information pertaining to a product. For example, physical and chemical aspects of a liquid may include but are not limited to internal non-intrusive properties (e.g., color, clarity, hue, saturation, value, reflection, fluorescence, absorption, etc.), and internal intrusive properties (e.g., viscosity, pH, molecular components, adhesion, cohesion spectrum, colorimetric assay, chemical sensors, combinatorial chemicals etc.). Additionally, external non-intrusive properties, such as those corresponding to external packaging and internal packaging, may be provided including but not limited to barcode, emblem, lot number, manufacturer logo, shape and color of package or vial, hologram, etc.

GAN training data module 62 comprises opposing neural networks that generate training data to improve the robustness of the drug dilution detection system, and automates expansion of a training data set. Once trained, the drug dilution detection system detects whether the product data corresponds to a real or counterfeit product.

GANs typically comprise at least two neural networks. For example, GAN training data module 62 may comprise a generator network that generates images and a discriminator network to classify the generated images as real or fake images. Initially, the discriminator network is trained on available drug dilution data, which may include real data, counterfeit data, and counterfeit dilution data. Once trained, the discriminator network is then used to analyze images produced by a generator network that correspond to counterfeit drug dilutions. As training of the opposing neural networks progresses, the generator network improves the quality of the computer generated counterfeit dilution images based on feedback from the discriminator network to expand training data and improve the robustness of the drug dilution detection system.

Drug dilution machine learning module 64 corresponds to the neural network deployed in operation to identify counterfeit diluted drugs. In some aspects, this system may correspond at least to the trained discriminator network, a neural network trained on training data from real, counterfeit, counterfeit-diluted training data as well as data generated from counterfeit-diluted generator (see, FIGS. 2 and 3) and from images generated by the generator network.

In other aspects, drug dilution machine learning module 64 may correspond to any machine learning model trained using the training data generated from real, counterfeit, counterfeit-diluted training data as well as data generated from counterfeit-diluted generator (see, FIGS. 2 and 3) and from images generated by the generator network.

Thus, in some aspects, the generative adversarial network may classify data from a product as real or counterfeit, and if counterfeit, may additionally provide information regarding the percentage of dilution. In other aspects, the data used to train the discriminator network may be provided to another machine learning system for training to detect counterfeit diluted drugs.

Dilution scoring module 66 provides an output to a user corresponding to the determination (e.g., real or counterfeit) of whether the liquid is real or diluted, as well as various metrics corresponding to the determination (e.g., accuracy, percentage of dilution, etc.). This module may comprise dilution percentage detector 357 (see, FIG. 2) that provides a determination as to the percentage dilution of the real product. Each of these modules are described in further detail throughout the application.

Measurement device 56 may include any suitable device for obtaining physical and/or chemical characteristics of the liquid drug. In some aspects, this may include pH meters, viscometers, spectrometer devices (e.g., mass spectrometer, nuclear magnetic resonance, etc.).

Image device 57 may include any suitable device for obtaining submicron images of the liquid drug. In some aspects, this may include an optical microscope that attaches or transmits data to a mobile device. In other aspects, this may include infrared machines, fluorescent microscopy devices, etc.

Figure 1B:
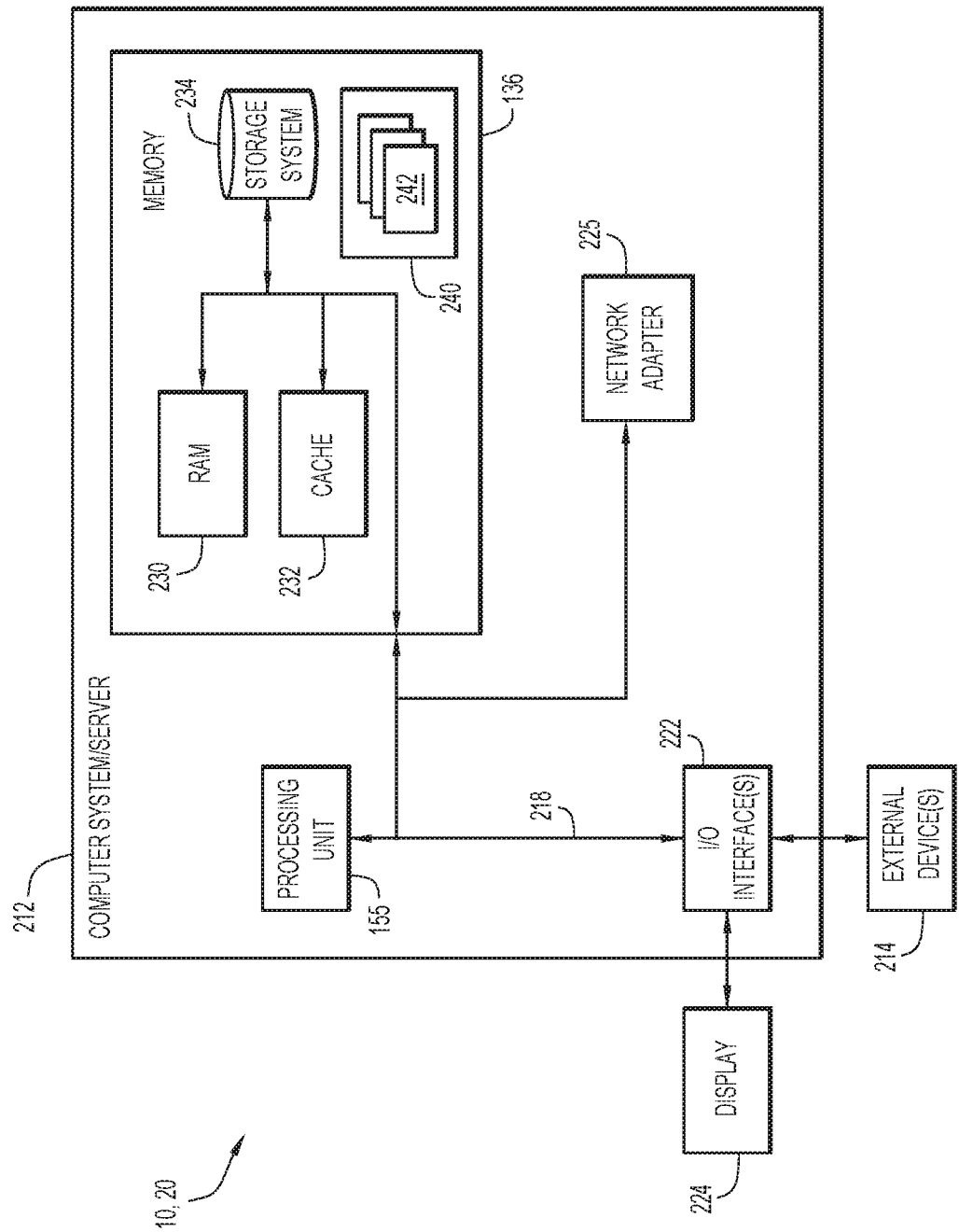
FIG. 1B is an example computing device for the computing environment of FIG. 1, according to an embodiment of the present invention.

Client systems 20 and server systems 10 may be implemented by any suitable computing device, such as computing device 212 shown in FIG. 1B for computing environment 100. This example is not intended to suggest any limitation as to the scope of use or functionality of embodiments of the invention described herein. Regardless, computing device 212 is capable of being implemented and/or performing any of the functionality set forth herein.

In the computing device, there is a computer system which is operational with numerous other general purpose or special purpose computing system environments or configurations. Examples of well-known computing systems, environments, and/or configurations that may be suitable for use with the computer system include, but are not limited to, personal computer systems, server computer systems, thin clients, thick clients, hand-held or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system 212 may be described in the general context of computer system executable instructions, such as program modules (e.g., drug dilution detection system 15 and its corresponding modules), being executed by a computer system. Generally, program modules may include routines, programs, objects, components, logic, data structures, and so on that perform particular tasks or implement particular abstract data types.

Computer system 212 is shown in the form of a general-purpose computing device. The components of computer system 212 may include, but are not limited to, one or more processors or processing units 155, a system memory 136, and a bus 218 that couples various system components including system memory 136 to processor 155.

Bus 218 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system 212 typically includes a variety of computer system readable media. Such media may be any available media that is accessible by computer system 212, and it includes both volatile and non-volatile media, removable and non-removable media.

System memory 136 can include computer system readable media in the form of volatile memory, such as random access memory (RAM) 230 and/or cache memory 232. Computer system 212 may further include other removable/non-removable, volatile/non-volatile computer system storage media. By way of example only, storage system 234 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 218 by one or more data media interfaces. As will be further depicted and described below, memory 136 may include at least one program product having a set (e.g., at least one) of program modules that are configured to carry out the functions of embodiments of the invention.

Program/utility 240, having a set (at least one) of program modules 242 (e.g., drug dilution detection system 15 and corresponding modules, etc.) may be stored in memory 136 by way of example, and not limitation, as well as an operating system, one or more application programs, other program modules, and program data. Each of the operating system, one or more application programs, other program modules, and program data or some combination thereof, may include an implementation of a networking environment. Program modules 242 generally carry out the functions and/or methodologies of embodiments of the invention as described herein.

Computer system 212 may also communicate with one or more external devices 214 such as a keyboard, a pointing device, a display 224, etc.; one or more devices that enable a user to interact with computer system 212; and/or any devices (e.g., network card, modem, etc.) that enable computer system 212 to communicate with one or more other computing devices. Such communication can occur via Input/Output (I/O) interfaces 222. Still yet, computer system 212 can communicate with one or more networks such as a local area network (LAN), a general wide area network (WAN), and/or a public network (e.g., the Internet) via network adapter 225. As depicted, network adapter 225 communicates with the other components of computer system 212 via bus 218. It should be understood that although not shown, other hardware and/or software components could be used in conjunction with computer system 212. Examples, include, but are not limited to: microcode, device drivers, redundant processing units, external disk drive arrays, RAID systems, tape drives, and data archival storage systems, etc.

Figure 2:
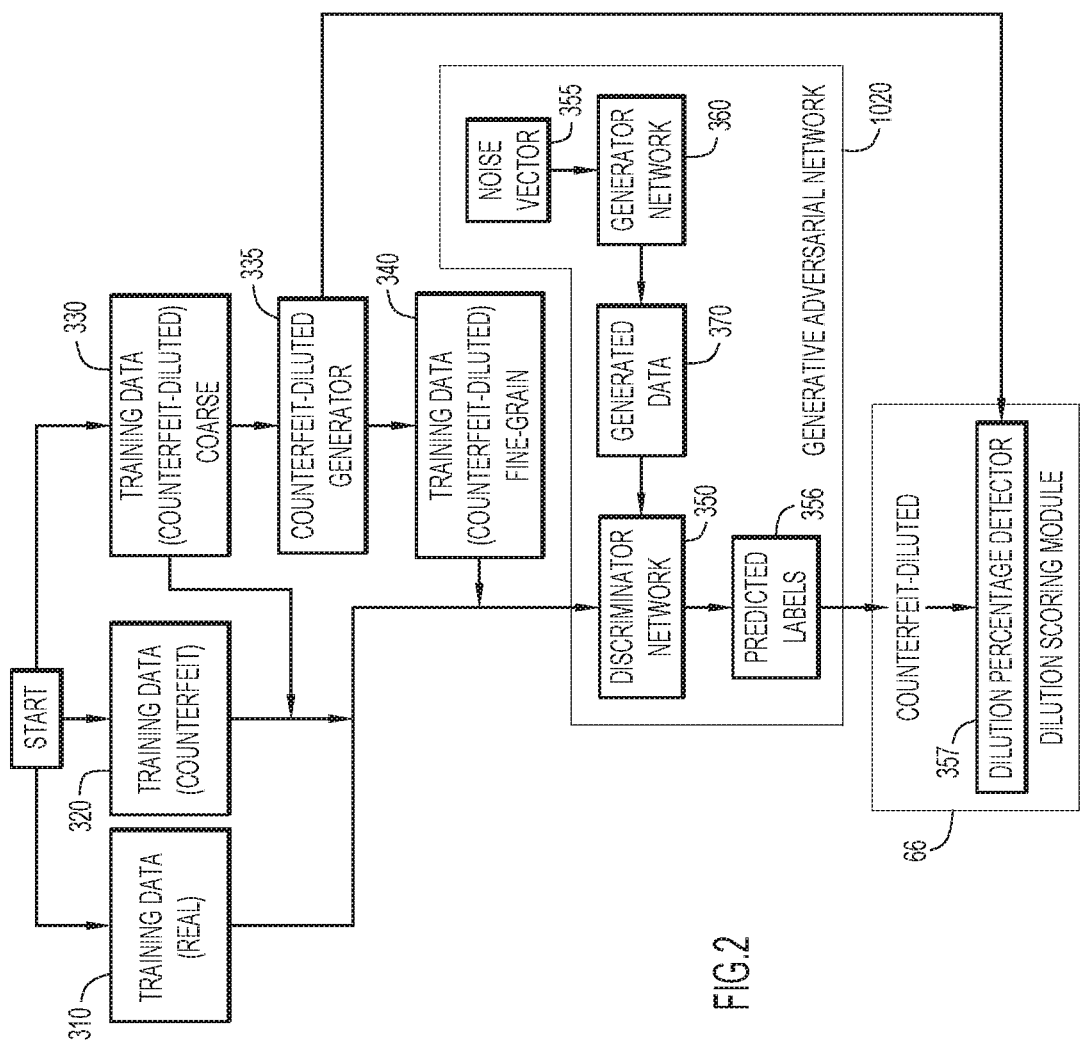
FIG. 2 is a flow diagram showing utilization of a generative adversarial network for drug dilution detection, according to an embodiment of the present invention.

FIG. 2 is a flow diagram corresponding to a drug dilution detection system comprising a generative adversarial network 1020 for liquid dilution analysis. Real training data 310, counterfeit training data 320, and counterfeit diluted training data 330 are provided to the drug dilution detection system 15. These data sets correspond to images of actual/real drugs, counterfeit drugs, as well as diluted counterfeit drug. The real training data 310 corresponds to images or measurements of the therapeutic that has not been diluted. The counterfeit training data 320 corresponds to images or measurements of the therapeutic that does not contain any drug (e.g., replaced with saline) or a chemically different substance that visually appears to be the same as the real drug. The counterfeit diluted training data 330 corresponds to images or measurements of the therapeutic that has undergone dilution (e.g., with saline or another suitable diluent). In aspects, images of counterfeit-diluted drugs may be obtained at graded/coarse dilution points (e.g., 25%, 50%, 75%, and 100%). The coarse grained counterfeit data collection 330 may be provided to counterfeit-diluted generator 335 (see FIG. 3), wherein the counterfeit-diluted generator 335 extrapolates the values of the coarse grained counterfeit dilution images to create a spectrum of progression of hue saturation values (HSVs). Based on the extrapolated values, training data comprising fine-grained images 340 are generated and provided to the discriminator network 350.

Once the training data has been collected and processed, it is provided to the generative adversarial network 1020, in which two simultaneous neural networks oppose each other, with one neural network (generator network 360) generating counterfeit dilution data 370 and the other neural network (discriminator network 350) discriminating as to whether the generated data is real. This system uses a probabilistic framework.

In an example embodiment, discriminator network 350, represented as a function D(Y), receives an input image, Y, and outputs a scalar value that indicates whether the image Y is real or counterfeit. The discriminator network may be trained based on training data 310, 320, 330, 340 and generated data 370. In some aspects, D(Y) is a function that produces a value within a first value range when Y is a real drug and produces a value within a second value range when Y is a counterfeit diluted or counterfeit drug. In aspects, D(Y) may produce a low value when Y is a real sample and a positive value when Y is a counterfeit sample. For images generated by generator network 360, a noise vector 355 may be provided to generator network 360, and generator network 360 may generate data 370 (e.g., images or data) based upon input from the noise vector. Generator network 360 comprises a generator function G(Z), where Z is a vector randomly sampled in a simple Gaussian distribution. The generator network 360 produces images to train discriminator network 350 D(Y) to have a first value range for real images and a second value range for counterfeit or counterfeit diluted images. For example, D(Y) may be trained to take the right shape, corresponding to a low value for real images and positive value for counterfeit images.

The discriminator network 350 receives the generated image, and classifies it as real, counterfeit, or counterfeit-diluted. Predicted labels 356 are generated (e.g., real, counterfeit, or counterfeit diluted) based on classification by the discriminator network, and when the machine learning system determines that the product is counterfeit-diluted, the dilution percentage detector 357 may generate a percentage dilution value provided from dilution scoring module 66. In some aspects, the dilution percentage detector determines the percentage of dilution value based upon extrapolated data generated by counterfeit diluted generator 335.

The generative adversarial network may function by minimizing the output of the discriminator network while the discriminator network is maximizing itself. When a real image is provided to the discriminator network, the discriminator network undergoes training and adjusts its parameters to minimize its output. Then, the discriminator network is provided with an image produced from the generator network, and the discriminator network adjusts its parameters to maximize its output D(G(Z)). However, the generator network G(Z) will train itself to produce images with a goal of having these images classified as counterfeit dilution images by the discriminator network. The generator network achieves this by optimizing the stochastic gradient of the discriminator network with respect to Y for each sample it produces. In other words, the stochastic gradient minimizes the output of D, while D is trying to maximize the gradient.

Suitably generated images, for example, generated images that are classified as counterfeit-dilutions, may be provided to any machine learning system to improve training of a drug dilution detection system for detecting diluted drugs.

Figure 3:
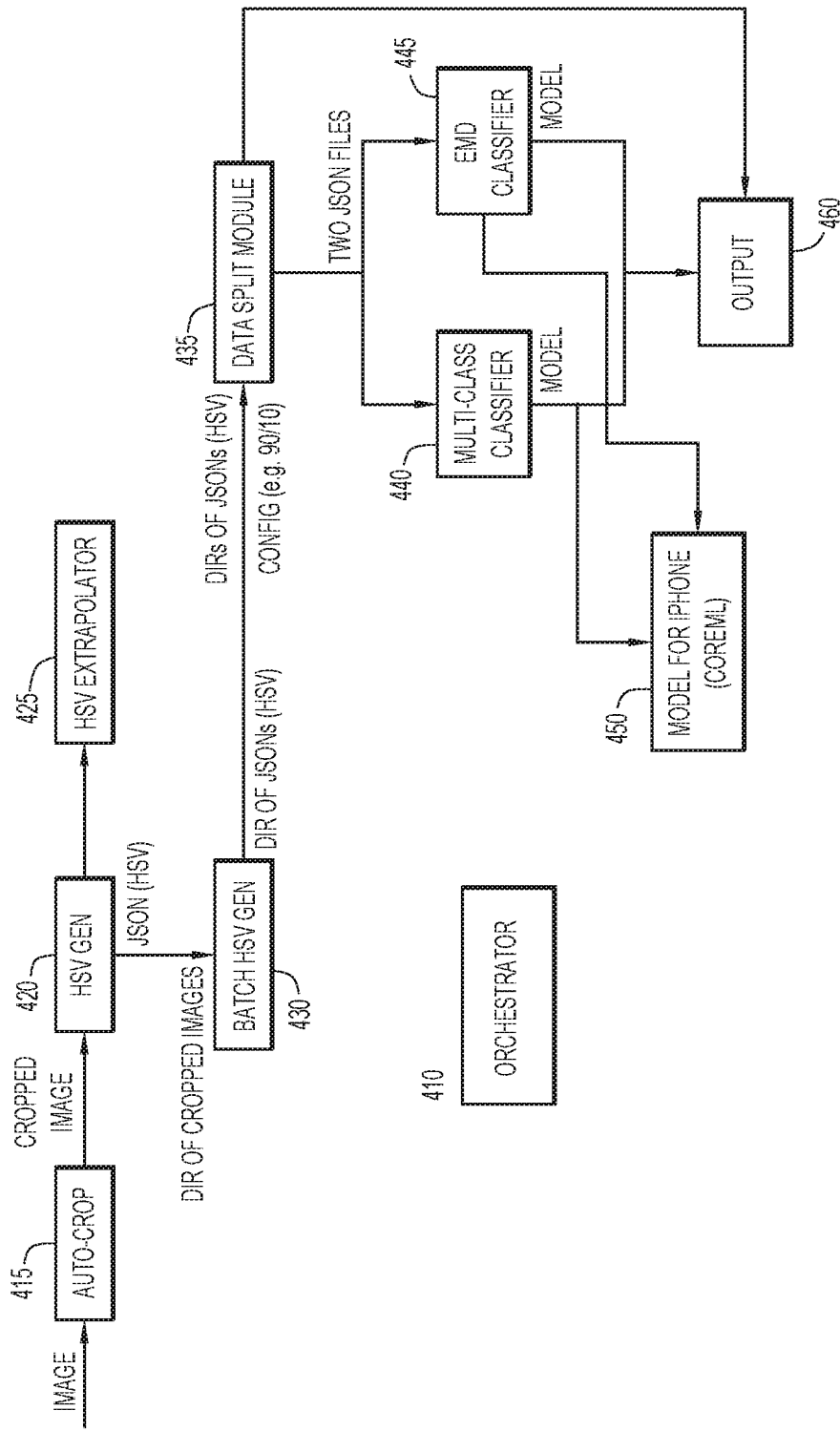
FIG. 3 is a more detailed flow diagram for generating counterfeit diluted images, according to an embodiment of the present invention.

FIG. 3 shows further example computational operations for the counterfeit diluted generator 335. An input image is cropped to generate auto-cropped image 415. Hue saturation values (HSV) are generated by HSV generator 420 based upon the provided images. The output of the HSV generator may be provided to HSV extrapolator 425 and to the batch HSV generator 430 (e.g., as JSON files). HSV extrapolator 425 uses estimation techniques to predict/generate data (e.g., HSV data) based on extending a known sequence of values. Thus, the HSV extrapolator generates dilution data apart from the GAN training data module. A directory of HSV values may be generated (e.g., a directory of JSON files) by the batch HSV generator and provided to data split module 435, which sends images to both multi-class classifier 440 and empirical mode decomposition (EMD) classifier 445. The output 460 of the multi-class classifier and EMD classifier are evaluated for accuracy and the output may also be provided to mobile device 450.

Orchestrator 410 manages automation of the dataflow. Since there are multiple classifiers and data generators (e.g., real data, extrapolated data, data generated from GAN modules), the orchestrator enables composability of the dataflow between these components.

Figure 4:
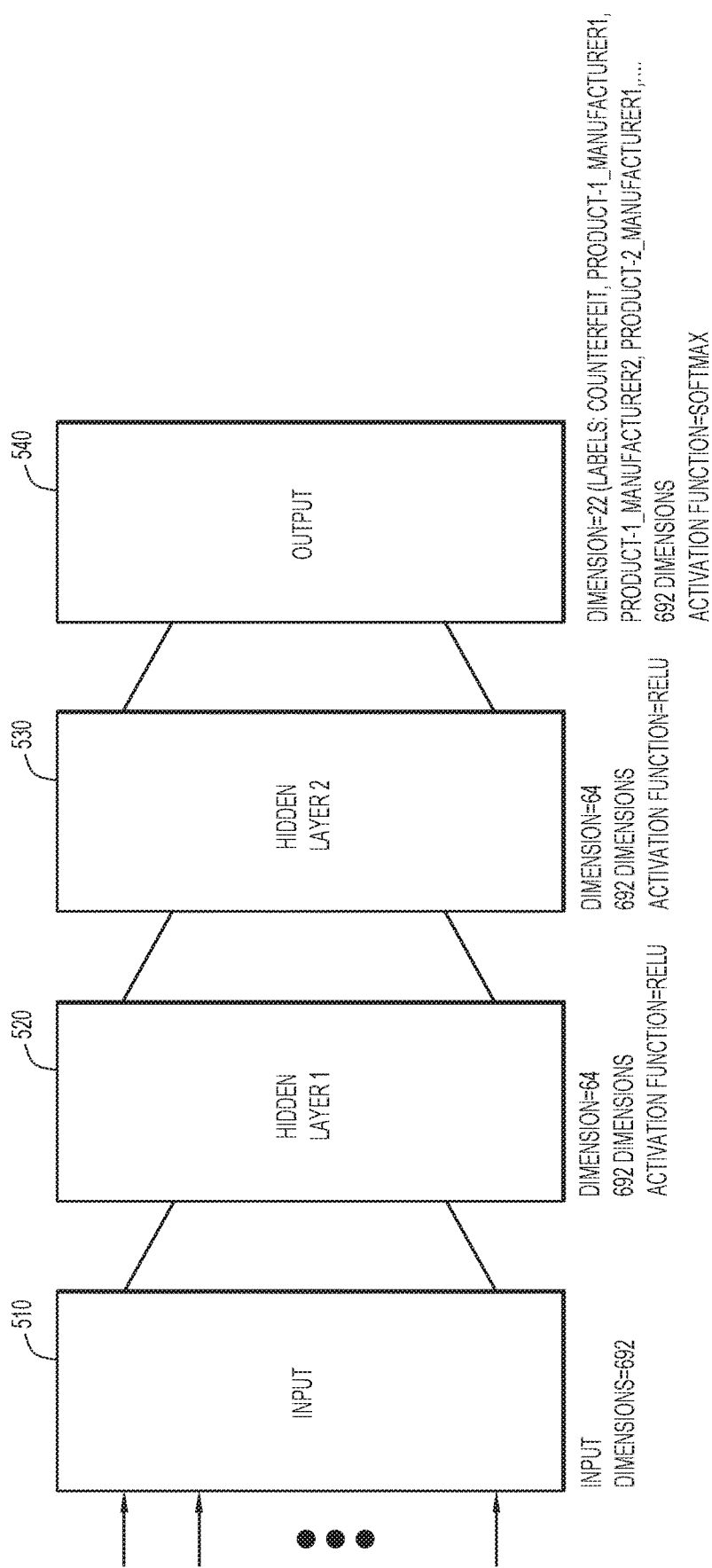
FIG. 4 shows an illustration of an example neural network for the drug dilution detection system, according to an embodiment of the present invention.

FIG. 4 shows an example illustration of a neural network (e.g., drug dilution detection machine learning module 64) for classification of an image. By way of example, the neural network may be a recurrent neural network with a plurality of hidden layers. Layer 510 corresponds to the input layer, with up to 692 dimensions. Layer 520 corresponds to a first hidden layer, with 692 dimensions. Layer 530 corresponds to a second hidden layer with 692 dimensions. The output layer 540 comprises the output (e.g., labels indicating whether the product is real or counterfeit or counterfeit diluted, also having 692 dimensions). Any suitable number of dimensions and layers may be selected for the machine learning models described herein.

The neural network may correspond to any neural network configured to perform classification of input data corresponding to a product into categories corresponding to real, counterfeit or counterfeit diluted drugs. In some aspects, this neural network may correspond to the discriminator network. In other aspects, this neural network may correspond to any suitably trained machine learning module based on the training data used to train the discriminator network.

In aspects, progressive gradation of images and measurements including external non-intrusive data, internal non-intrusive data, and internal intrusive data may be performed to provide a more comprehensive and accurate analysis than contemporary approaches.

In aspects, progressive analysis comprises analyzing, by the drug dilution detection system, product characteristics corresponding to external non-intrusive data. Based on analysis of the external non-intrusive data, features for internal non-intrusive data may be determined. Based on analysis of the internal non-intrusive data, features for internal intrusive data may be determined. In aspects, features of any of these categories may be used to predict features of other related categories. For example, upon receipt of a product, the system may first analyze the packaging to determine whether the packaging is real or counterfeit. The product may be removed from its external packaging, and the container (if applicable) encapsulating the product may be analyzed for authenticity. Finally, the therapeutic product may be analyzed directly to determine whether it is authentic or counterfeit. Thus, these techniques provide multiple levels of progressive analysis to determine a product's authenticity. This approach provides for a comprehensive and progressive analysis to be performed to determine whether a product is real or counterfeit.

Figure 5A:
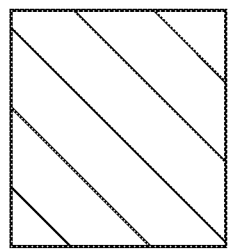
FIGS. 5A-5D show illustrations and graphs related to generating training data to train a drug dilution detection system, according to an embodiment of the present invention.
Figure 5A:
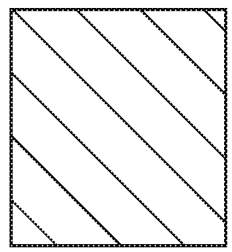
Figure 5A:
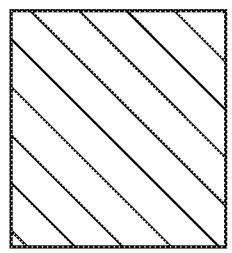
Figure 5A:
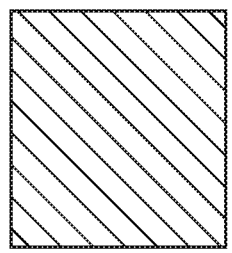
Figure 5A:
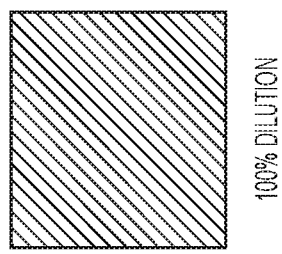
Figure 5B:
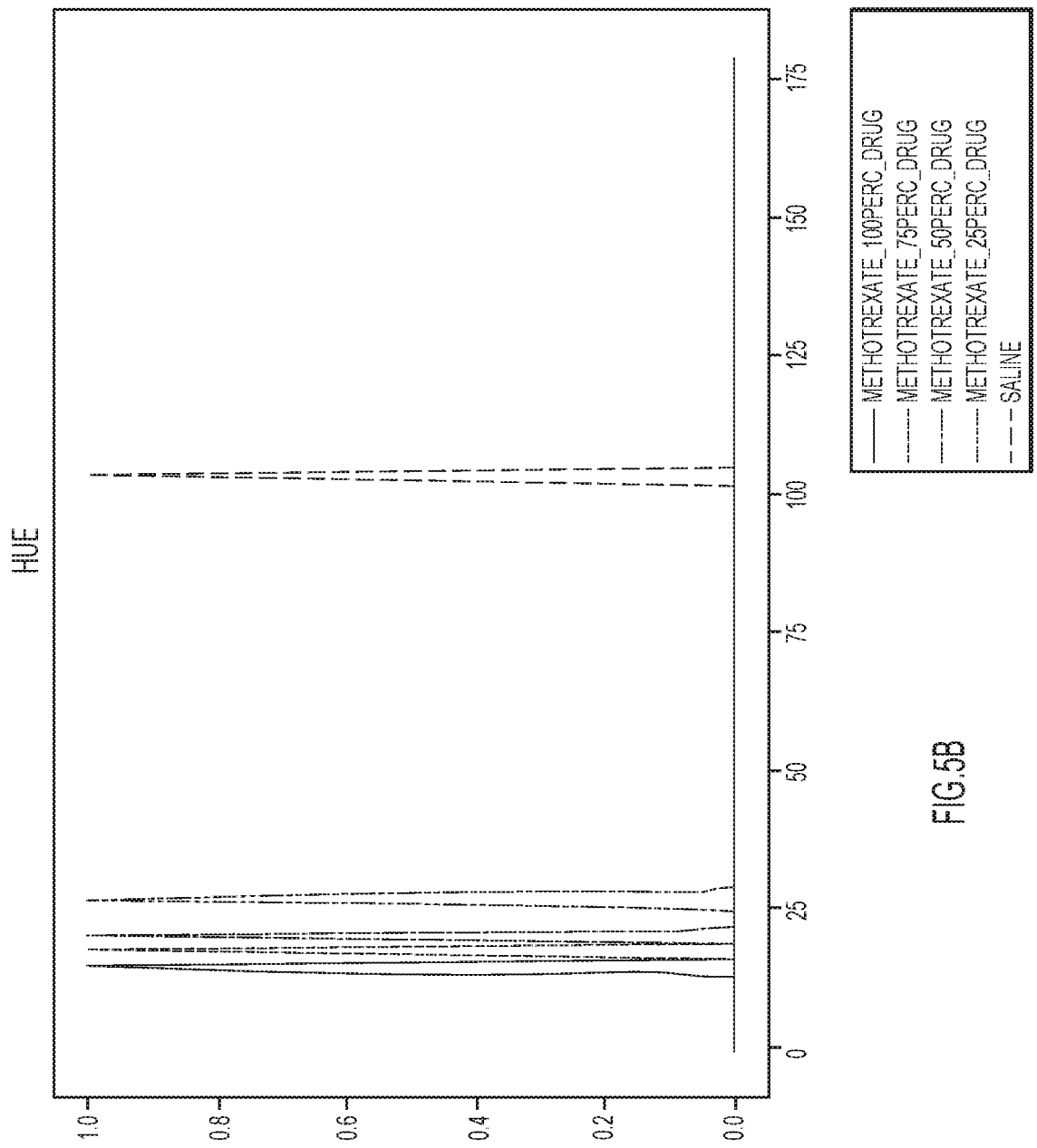
Figure 5C:
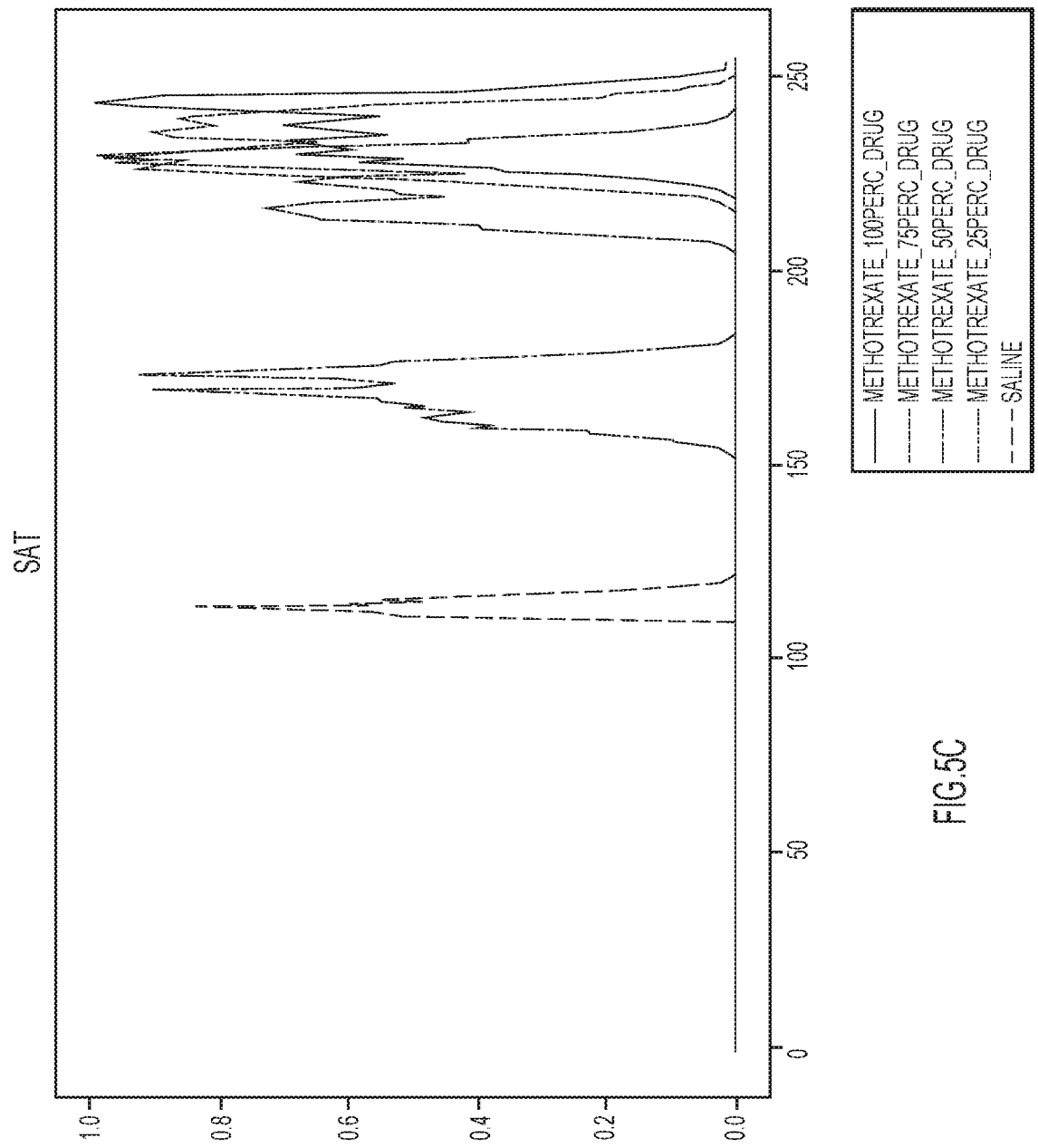
Figure 5D:
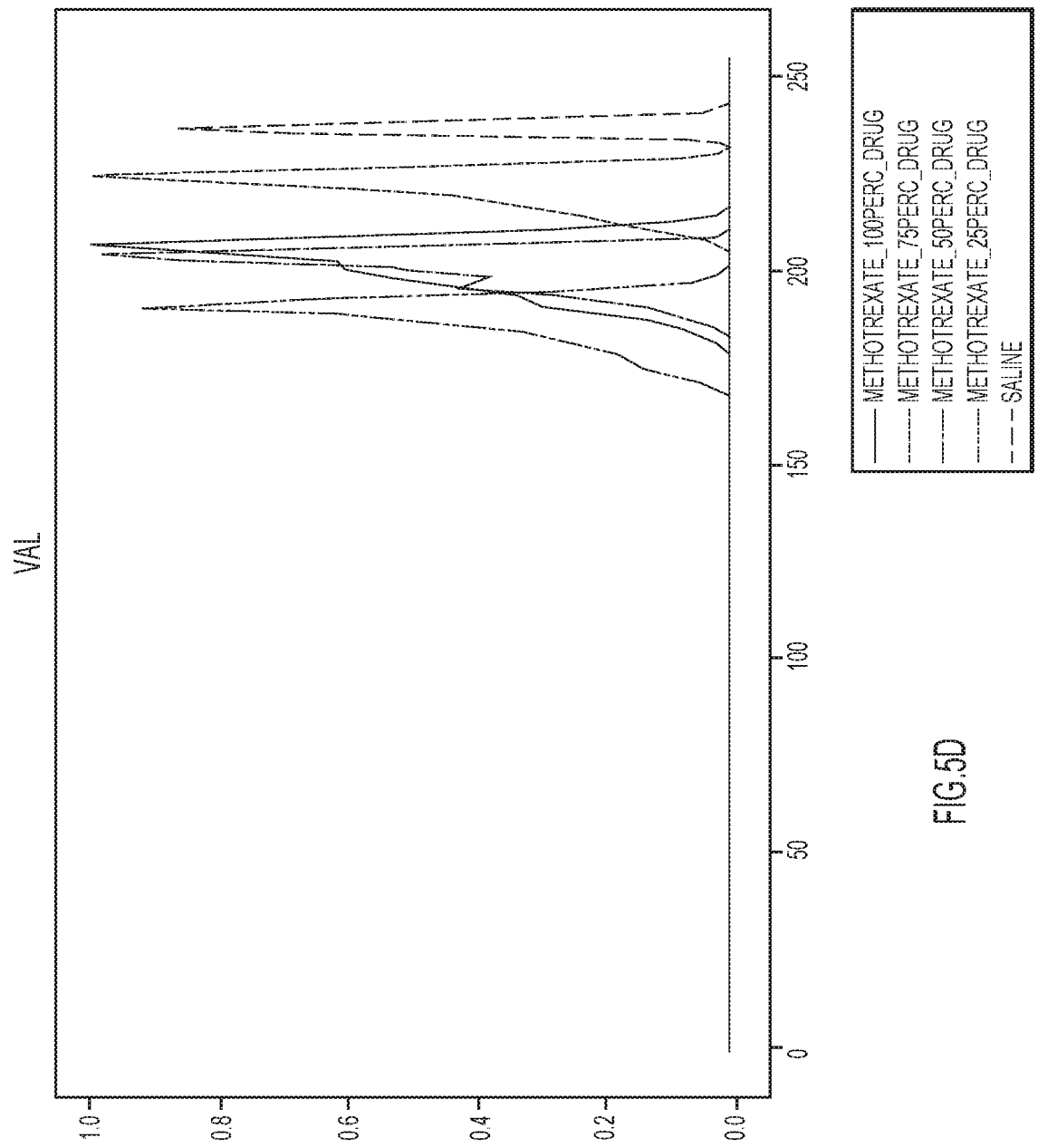

FIGS. 5A-5D show illustrations of dilutions of a pharmaceutical compound, methotrexate. FIG. 5A shows a colorimetric HSV map of methotrexate, ranging from 0% dilution (pure methotrexate on the left), various dilutions with saline of 25% 50% and 75% in between, and 100% dilution (pure saline on the right). This coarse grained data may be provided to the counterfeit-diluted generated 335 to generate fine grained images. Both the fine grained images and the coarse grained images may be provided to the GAN for training. FIG. 5B shows variations in hue (angle of color) as a function of saline dilution. FIG. 5C shows variations in saturation (amount of color) as a function of saline dilution. FIG. 5D shows variations in value (brightness of color) as a function of saline dilution. Together, HSV corresponds to a color model for detecting liquids.

FIG. 6 is an operational flow chart showing high-level operations of the techniques provided herein for detecting diluted drugs using machine learning. At operation 710, measurements and images corresponding to a product are obtained, wherein the product is formulated as a liquid, and wherein the measurements and images capture physical, spectral, optical, and/or chemical properties of the product. At operation 720, the measurements and images are provided to a machine learning model, wherein the machine learning model is trained using data generated from a generative adversarial network. At operation 730, the machine learning model detects whether the product is a real or counterfeit product.

Present techniques utilize GANs to generate training data that results in a robust drug dilution detection system. The GANs are used to generate counterfeit dilution data, which increases the number of images in the training data set and provides more variability in the training data, leading to a more robust drug dilution detection system. Training data acquisition can be achieved by physical or logical approaches. Obtaining physical data is often complex and time consuming, and often costly due to drug costs (e.g., for chemotherapy and immunotherapy drugs), supervision cost (e.g., oncology personnel for handling and supervision), and cost/effort of capturing a wide spectrum of variations/dilutions. These systems may be used to validate drugs for administration to patients, detect counterfeit or counterfeit diluted drugs, as well as streamline generation of a robust drug dilution detection model.

These techniques may be applied to a wide variety of environments, including pharmaceutical industry, beverage and food industry, oil and gas industry, etc.

It will be appreciated that the embodiments described above and illustrated in the drawings represent only a few of the many ways of implementing embodiments for drug dilution detection and generating training data from GANs for training drug dilution detection systems.

The environment of the present invention embodiments may include any number of computer or other processing systems (e.g., client or end-user systems, server systems, etc.) and databases or other repositories arranged in any desired fashion, wherein the present invention embodiments may be applied to any desired type of computing environment (e.g., cloud computing, client-server, network computing, mainframe, stand-alone systems, etc.). The computer or other processing system employed by the present invention embodiments may be implemented by any number of any personal or other type of computer or processing system (e.g., desktop, laptop, PDA, mobile devices, etc.), and may include any commercially available operating system and any combination of commercially available and custom software (e.g., browser software, communications software, server software, drug dilution detection system 15, etc.). These systems may include any type of monitors and input devices (e.g., keyboard, mouse, voice recognition, etc.) to enter and/or view information.

It is to be understood that the software (e.g., drug dilution detection system 15, including image and measurement data 60, GAN training data module 62, drug dilution machine learning module 64, dilution scoring module 66, etc.) of the present invention embodiments may be implemented in any desired computer language and could be developed by one of ordinary skill in the computer arts based on the functional descriptions contained in the specification and flowcharts illustrated in the drawings. Further, any references herein of software performing various functions generally refer to computer systems or processors performing those functions under software control. The computer systems of the present invention embodiments may alternatively be implemented by any type of hardware and/or other processing circuitry.

The various functions of the computer or other processing systems may be distributed in any manner among any number of software and/or hardware modules or units, processing or computer systems and/or circuitry, where the computer or processing systems may be disposed locally or remotely of each other and communicate via any suitable communications medium (e.g., LAN, WAN, Intranet, Internet, hardwire, modem connection, wireless, etc.). For example, the functions of the present invention embodiments may be distributed in any manner among the various end-user/client and server systems, and/or any other intermediary processing devices. The software and/or algorithms described above and illustrated in the flowcharts may be modified in any manner that accomplishes the functions described herein. In addition, the functions in the flowcharts or description may be performed in any order that accomplishes a desired operation.

The software of the present invention embodiments (e.g., drug dilution detection system 15, including image and measurement data 60, GAN training data module 62, drug dilution machine learning module 64, dilution scoring module 66, etc.) may be available on a non-transitory computer useable medium (e.g., magnetic or optical mediums, magneto-optic mediums, floppy diskettes, CD-ROM, DVD, memory devices, etc.) of a stationary or portable program product apparatus or device for use with stand-alone systems or systems connected by a network or other communications medium.

The communication network may be implemented by any number of any type of communications network (e.g., LAN, WAN, Internet, Intranet, VPN, etc.). The computer or other processing systems of the present invention embodiments may include any conventional or other communications devices to communicate over the network via any conventional or other protocols. The computer or other processing systems may utilize any type of connection (e.g., wired, wireless, etc.) for access to the network. Local communication media may be implemented by any suitable communication media (e.g., local area network (LAN), hardwire, wireless link, Intranet, etc.).

The system may employ any number of any conventional or other databases, data stores or storage structures (e.g., files, databases, data structures, data or other repositories, etc.) to store information (e.g., classifications, accuracy, generated training data, physical/chemical/spectral/optical drug characterization data, fine and coarse grained drug dilution data, etc.). The database system may be implemented by any number of any conventional or other databases, data stores or storage structures (e.g., files, databases, data structures, data or other repositories, etc.) to store information (e.g., classifications, accuracy, generated training data, physical/chemical/spectral/optical drug characterization data, fine and coarse grained drug dilution data, etc.). The database system may be included within or coupled to the server and/or client systems. The database systems and/or storage structures may be remote from or local to the computer or other processing systems, and may store any desired data (e.g., classifications, accuracy, generated training data, physical/chemical/spectral/optical drug characterization data, fine and coarse grained drug dilution data, etc.).

The present invention embodiments may employ any number of any type of user interface (e.g., Graphical User Interface (GUI), command-line, prompt, etc.) for obtaining or providing information (e.g., classifications, accuracy, generated training data, physical/chemical/spectral/optical drug characterization data, fine and coarse grained drug dilution data, etc.), wherein the interface may include any information arranged in any fashion. The interface may include any number of any types of input or actuation mechanisms (e.g., buttons, icons, fields, boxes, links, etc.) disposed at any location to enter/display information and initiate desired actions via any suitable input devices (e.g., mouse, keyboard, etc.). The interface screens may include any suitable actuators (e.g., links, tabs, etc.) to navigate between the screens in any fashion.

The output of the drug dilution detection system 15 may include any information arranged in any fashion, and may be configurable based on rules or other criteria to provide desired information to a user (e.g., classifications, accuracy, generated training data, physical/chemical/spectral/optical drug characterization data, fine and coarse grained drug dilution data, etc.).

The present invention embodiments are not limited to the specific tasks or algorithms described above, but may be utilized for any application in which a GAN may be used to create robust training data. Further, this approach may be generally applicable to providing support in any context, and is not limited to any particular application domain, such as clinical, investigation, biomedical, research-oriented, manufacturing, etc.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises", "comprising", "includes", "including", "has", "have", "having", "with" and the like, when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be accomplished as one step, executed concurrently, substantially concurrently, in a partially or wholly temporally overlapping manner, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

What is claimed is:

1. A method of detecting drugs or chemicals that have been diluted using machine learning comprising:
    obtaining measurements and images corresponding to a product, wherein the product is formulated as a liquid, and wherein the measurements and images capture properties of the product;
    providing the measurements and images to a machine learning model, wherein the machine learning model is trained using data generated from a learning network comprising a plurality of interacting learning models with contradictory objectives, and wherein at least one of the plurality of interacting learning models is trained using information derived from images obtained from diluted drugs corresponding to actual drugs that have been diluted by a diluent at a plurality of dilution points; and
    detecting whether the product is a real or counterfeit product.

2. The method of claim 1, wherein the plurality of interacting learning models comprises a discriminator network and a generator network, and further comprising:
    training the discriminator network using training data derived from real drugs, counterfeit drugs, and coarse grained images obtained from the diluted drugs;
    generating counterfeit-dilution data by the generator network; and
    when the generated counterfeit-dilution data meets specified classification criteria by the generator network, including the generated counterfeit-dilution data in the training data for the discriminator network.

3. The method of claim 2, further comprising:
    providing a noise vector to the generator network; and
    injecting noise into data produced by the generator network based on the noise vector.

4. The method of claim 2, further comprising:
    training the discriminator network using training data derived from coarse grained data and fine grained data, wherein the fine grained data is obtained from extrapolating information from the coarse grained data.

5. The method of claim 2, further comprising:
    determining a counterfeit-dilution percentage value for a product;
    determining a dosage or an efficacy based on the counterfeit-dilution percentage value; and
    when a reference efficacy or a prescribed dosage is less than the determined efficacy or dosage, sending an alert that the product is counterfeit-diluted.

6. The method of claim 1, further comprising:
    performing progressive analysis by analyzing product characteristics corresponding to external non-intrusive data, determining features for internal non-intrusive data, and determining features for internal intrusive data; and detecting whether the product is a real, counterfeit or counterfeit-diluted product based on the progressive analysis.

7. The method of claim 1, wherein the data generated by the plurality of interactive learning models are used to train another machine learning model.

8. A system to detect drugs or chemicals that have been diluted using machine learning, the system comprising:
one or more computer processors;
one or more computer readable storage media;
program instructions stored on the one or more computer readable storage media for execution by at least one of the one or more computer processors, the program instructions comprising instructions to:
receive measurements and images corresponding to a product, wherein the product is formulated as a liquid, and wherein the measurements and images capture properties of the product;
provide the measurements and images to a machine learning model, wherein the machine learning model is trained using data generated from a learning network comprising a plurality of interacting learning models with contradictory objectives, and wherein at least one of the plurality of interacting learning models is trained using information derived from images obtained from diluted drugs corresponding to actual drugs that have been diluted by a diluent at a plurality of dilution points; and
detect whether the product is a real or counterfeit product.

9. The system of claim 8, wherein the plurality of interactive learning models comprises a discriminator network and a generator network, and wherein the program instructions further comprise instructions to:
train the discriminator network using training data derived from real drugs, counterfeit drugs, and coarse grained images obtained from the diluted drugs;
generate counterfeit-dilution data by the generator network; and
when the generated counterfeit-dilution data meets specified classification criteria by the generator network, include the generated counterfeit-dilution data in the training data for the discriminator network.

10. The system of claim 9, wherein the program instructions further comprise instructions to:
provide a noise vector to the generator network; and
inject noise into data produced by the generator network based on the noise vector.

11. The system of claim 9, wherein the program instructions further comprise instructions to:
train the discriminator network using training data derived from coarse grained data and fine grained data, wherein the fine grained data is obtained from extrapolating information from the coarse grained data.

12. The system of claim 9, wherein the program instructions further comprise instructions to:
determine a counterfeit-dilution percentage value for a product;
determine a dosage or an efficacy based on the counterfeit-dilution percentage value; and
when a reference efficacy or a prescribed dosage is less than the determined efficacy or dosage, send an alert that the product is counterfeit-diluted.

13. The system of claim 9, wherein the program instructions further comprise instructions to:
perform progressive analysis by analyzing product characteristics corresponding to external non-intrusive data, determining features for internal non-intrusive data, and determining features for internal intrusive data; and
detect whether the product is a real, counterfeit or counterfeit-diluted product based on the progressive analysis.

14. The system of claim 8, wherein the data generated by the plurality of interacting learning models is used to train another machine learning model.

15. A computer program product to detect drugs or chemicals that have been diluted using machine learning, the computer program product comprising one or more computer readable storage media collectively having program instructions embodied therewith, the program instructions executable by a computer to cause the computer to:
receive measurements and images corresponding to a product, wherein the product is formulated as a liquid, and wherein the measurements and images capture properties of the product;
provide the measurements and images to a machine learning model, wherein the machine learning model is trained using data generated from a learning network comprising a plurality of interacting learning models with contradictory objectives, and wherein at least one of the plurality of interacting learning models is trained using information derived from images obtained from diluted drugs corresponding to actual drugs that have been diluted by a diluent at a plurality of dilution points; and
detect whether the product is a real or counterfeit product.

16. The computer program product of claim 15, wherein the plurality of interactive learning models comprises a discriminator network and a generator network, and wherein the program instructions further comprise instructions to:
train the discriminator network using training data derived from real drugs, counterfeit drugs, and coarse grained images obtained from the diluted drugs;
generate counterfeit-dilution data by the generator network; and
when the generated counterfeit-dilution data meets specified classification criteria by the generator network, include the generated counterfeit-dilution data in the training data for the discriminator network.

17. The computer program product of claim 16, wherein the program instructions further comprise instructions to:
provide a noise vector to the generator network; and
inject noise into data produced by the generator network based on the noise vector.

18. The computer program product of claim 16, wherein the program instructions further comprise instructions to:
train the discriminator network using training data derived from coarse grained data and fine grained data, wherein the fine grained data is obtained from extrapolating information from the coarse grained data.

19. The computer program product of claim 16, wherein the program instructions further comprise instructions to:
determine a counterfeit-dilution percentage value for a product;
determine a dosage or an efficacy based on the counterfeit-dilution percentage value; and
when a reference efficacy or a prescribed dosage is less than the determined efficacy or dosage, send an alert that the product is counterfeit-diluted.

20. The computer program product of claim 16, wherein the program instructions further comprise instructions to:
perform progressive analysis by analyzing product characteristics corresponding to external non-intrusive data, determining features for internal non-intrusive data, and determining features for internal intrusive data; and
detect whether the product is a real, counterfeit or counterfeit-diluted product based on the progressive analysis.

\* \* \* \* \*